(12) United States Patent
Gidon

(10) Patent No.: US 8,306,306 B2
(45) Date of Patent: Nov. 6, 2012

(54) DEVICE FOR CHARACTERIZING UNIQUE OBJECTS

(75) Inventor: Serge Gidon, La Murette (FR)

(73) Assignee: Commissariat a l'Energie Atomique, Paris (FR)

( * ) Notice: Subject to any disclaimer, the term of this patent is extended or adjusted under 35 U.S.C. 154(b) by 699 days.

(21) Appl. No.: 12/375,983

(22) PCT Filed: Aug. 1, 2007

(86) PCT No.: PCT/EP2007/057956
§ 371 (c)(1),
(2), (4) Date: Mar. 12, 2009

(87) PCT Pub. No.: WO2008/015230
PCT Pub. Date: Feb. 7, 2008

(65) Prior Publication Data
US 2009/0316979 A1    Dec. 24, 2009

(30) Foreign Application Priority Data
Aug. 2, 2006 (FR) .................................. 06 53248

(51) Int. Cl.
*G06K 9/00* (2006.01)
*G01B 11/02* (2006.01)
*G01B 11/14* (2006.01)

(52) U.S. Cl. .................. 382/141; 356/496; 356/625

(58) Field of Classification Search ............. 82/100–154
See application file for complete search history.

(56) References Cited

U.S. PATENT DOCUMENTS

| | | | | |
|---|---|---|---|---|
| 3,782,827 A * | 1/1974 | Nisenson et al. | ............ | 356/600 |
| 4,828,392 A * | 5/1989 | Nomura et al. | ............ | 356/401 |
| 5,428,442 A * | 6/1995 | Lin et al. | ............ | 356/237.5 |
| 5,463,459 A * | 10/1995 | Morioka et al. | ............ | 356/237.5 |
| 5,471,066 A * | 11/1995 | Hagiwara | ............ | 250/559.48 |
| 5,880,838 A | 3/1999 | Marx et al. | | |
| 6,750,968 B2 * | 6/2004 | Sandusky | ............ | 356/369 |
| 2003/0227623 A1* | 12/2003 | Zhan et al. | ............ | 356/369 |
| 2004/0004726 A1 | 1/2004 | Sezginer et al. | | |
| 2006/0033921 A1 | 2/2006 | Den Boef et al. | | |

(Continued)

FOREIGN PATENT DOCUMENTS

EP    1 628 164    2/2006

(Continued)

OTHER PUBLICATIONS

Christian Brosseau, "Fundamentals of Polarized Light: A Statistical Optics Approach", ("Mueller Matrix Analysis of Light Depolarization by a Linear Optical medium"), Wiley-Interscience, Oct. 1, 1998, pp. 235-243 and 350-356.

(Continued)

*Primary Examiner* — Gregory J Toatley
*Assistant Examiner* — Jarreas C Underwood
(74) *Attorney, Agent, or Firm* — Oblon, Spivak, McClelland, Maier & Neustadt, L.L.P.

(57) ABSTRACT

An examination method of a unique object including: forming a coherent radiation beam using a coherent source, illuminating the object by the coherent radiation beam, focussed using a focussing mechanism positioned directly in contact with the object or in a very close position to the object, and forming, using a detection mechanism, the optical Fourier transform image of the light diffracted by the object.

28 Claims, 4 Drawing Sheets

U.S. PATENT DOCUMENTS

2006/0066855 A1 3/2006 Boef et al.
2006/0119913 A1* 6/2006 Moon .............................. 359/2
2007/0064247 A1 3/2007 Petit et al.

FOREIGN PATENT DOCUMENTS

WO 2005 026707 3/2005

OTHER PUBLICATIONS

Boher, P. et al., "Innovative Rapid Photo-goniometry method for CD metrology", Proceedings of SPIE, vol. 5375, No. 1, pp. 1302-1313, XP-002315685, (May 2004).

Ghislain, L. P. et al., "Near-field photolithography with a solid immersion lens", Applied Physics Letters, vol. 74, No. 4, pp. 501-503, XP012023099, (Jan. 25, 1999).

Allgair, J. et al., "Spectroscopic Critical Dimension (SCD) Metrology for CD Control and Stepper Characterization", KLA-Tencor Corporation, http://www.kla-tencor.com/company/magazine/fal101/SCD.pdf, pp. 50-54, (Fall 2001).

Boher, P. et al., "Innovative Rapid Photo-goniometry method for CD metrology", http://www.eldim.fr/ezcontrast/semiconductor.htm, pp. 1-12, (May 2004).

* cited by examiner

DEVICE FOR CHARACTERIZING UNIQUE OBJECTS

FIELD OF THE INVENTION AND STATE OF THE RELATED ART

The invention relates to the field of characterisation—particularly applied for the purposes of microelectronics—which makes it possible to determine the shapes of patterns on the surface of a substrate. This technique enables characterisation on a so-called "unique" isolated object.

Lithography, combined with deposition and etching techniques, makes it possible to "transfer", by means of an optical process, the image of a mask, whereon patterns are represented, in a resin deposited on the very surface of substrates. The resin, once insolated, is developed and generally serves as a mask for etching and/or deposition processes used to carry out integrated circuit production steps.

The quality of photoetching methods is tested, in production lines, by means of various referenced characterisation methods such as "Critical Dimension Metrology". It is endeavoured to measure nanometric dimensions (up to 100 nm) with precisions of the order of a few per cent.

One solution is to observe a cross-section of the patterns with an SEM (scanning electron microscope). This approach has the drawback of being destructive and not very fast. Similarly, the AFM (atomic force microscope) technique, although it is non-destructive, is time-consuming.

The technique referred to as "Scaterometry" consists of observing the diffraction induced by periodic structures designed specifically for characterisation purposes on the substrate. Said patterns are periodic and behave like gratings, wherein the intensity of the various degrees of diffraction as a function of the angles of incidence is analysed. This analysis may be carried out by means of correlation of the measurements with a catalogue of calculated theoretical diffraction data. Another possibility is to perform a reverse regression of the data to try to deduce the key parameters of an expected shape model.

The scaterometric technique is implemented in various ways. One of the methods consists of a goniometric analysis of the diffraction of the gratings illuminated by a directive source [Spectroscopic Critical Dimension (SCD) Metrology for CD Control and Stepper Characterization, John Allgair, KLA-Tencor Corporation, http://www.kla-tencor.com/company/magazine/fall01/SCD.pdf]. This technique is restricted by the data acquisition time which requires the mechanical movement of the detectors.

Another approach consists of making their recording in an integrated manner, by means of an optical system which forms, on an image detector, mapping of the light intensity along two spatial angles, azimuth and declination [http://www.eldim.fr/ezcontrast/semiconductor.htm.].

In fact, the optical system produces, on the detector, the image of the "Fourier plane" of the characterisation grating.

In this type of device, the source used is "extended" and positioned in the Fourier plane of the object grating. Under these conditions, the object grating is illuminated with more or less parallel light beams with respect to each other.

Although the scaterometry technique has proved its merits and is used on a daily basis, it is confronted with the need to produce specific characterisation patterns, forming gratings, which, on one hand, occupy a specific position on the wafers or the substrates and, on the other, cannot be placed in any position.

This is a problem in that, conversely, it is increasingly desired to increase the occupancy rate of the surface of each substrate. In addition, the problem arises of finding a method that can be implemented in all the zones or all the parts of a substrate.

The problem also arises of being able to identify the presence and the shape of any pattern on the surface of a substrate.

DESCRIPTION OF THE INVENTION

The invention relates to a new scaterometry technique, which makes it possible to make measurements on so-called "unique" objects. These may be lines or contact blocks that can be found at any point on a surface of a substrate and which result from the implementation of a microtechnology or microelectronic method. Said lines or contact blocks do not need to be specifically provided for, unlike the characterisation grids used in techniques according to the prior art.

According to the invention, the infinite diffraction figure generated by such a unique object is observed by means of an optical system. An examination method according to the invention comprises:

the illumination of the object, and of a part of a substrate whereon it is formed, by means of a spatially coherent light beam, preferentially from a directive source optical system, focussed on the object with a high numerical aperture, the formation of the image of the optical FT (Fourier transform) of the light diffracted by the object.

The diffraction figure obtained, and therefore the optical FT thereof, is closely dependent on the object. For example, said object is a block, having a rectangular or rounded shape, or a strip, having an elongated shape, or a channel having a rectangular or rounded cross-section.

Therefore, the present invention relates to the analysis of a "unique" object on the surface of a substrate using a beam from a coherent source focussed with high numerical aperture focussing means (between 0.5 and 1.8 or 3). This aperture depends on the index of the medium in question and the angle of acceptance of the focussing means.

This combination between a coherent source and high numerical aperture focussing means makes it possible to produce all the incidences on the object simultaneously. With the maximum aperture, or with a high aperture, work is performed on a very small zone of the object and the surrounding substrate. In this way, this avoids having to use means to select a specific incidence.

The invention also relates to a device for the measurement of dimensional and/or structural characteristics of a unique object, comprising:

means to illuminate the object by means of a coherent light beam, high numerical aperture focussing means, to focus said beam on the object and a part of the surrounding substrate, means to form the image of the optical Fourier transform of the light diffracted by the object and by the part of the substrate which is illuminated around the object; the illuminated assembly will hereinafter be referred to as "object".

The high numerical aperture focussing means, or a part of said means, may be positioned directly in contact with the object or in a very close position to the object. The distance between the object and said focussing means is preferentially less than a few dozen nm, for example less, in air, than 10 nm or 30 nm or 50 nm or, in the presence of a fluid film, than 100 nm.

An interface, or index adaptation, liquid, may be arranged between the object and the lens. The distance between same is in this case approximately 30 nm to 100 nm.

The lens is for example a solid immersion lens, wherein the proximity with respect to the object and the index will make it possible to work with a high numerical aperture.

In addition, the use of focussing means or a lens close to the object makes it possible to work at an effective analysis wavelength, on the object, equal to a fraction of the source wavelength. This use of a lower wavelength makes it possible to analyse objects with small characteristic dimensions easily.

The source is preferentially a directive source, or having a narrow geometric range (in optical terms, i.e. having both a reduced surface area and low divergence), for example a bright source such as a laser or LED. Polarisation means make it possible to work in polarised incident light. The focussing of the source on the object defines the zone illuminated thereon and on a part of the substrate surrounding the same. Therefore, the definition of said illuminated zone does not require means such as a diaphragm arranged on the trajectory in the direction of the object.

The analysis means, or means for forming the image of the OFT of the light diffracted or reflected by the object, make it possible to establish the conjugation of the plane of the object and the plane of the Fourier transform thereof. Detection of one or more polarisation state(s) of the beam reflected or diffracted by the object may be carried out. In this way, polarisation means of such a beam may be provided, enabling an analysis of various polarisations if applicable.

The diffraction figures obtained being highly characteristic of the object, processing may be performed at the detector output; viewing the diffracted field figures alone enables a first characterisation. Digital processing may also make it possible to determine an outline of the shape of the unique object.

It is possible to eliminate the "speckle" phenomenon, inherent to coherent light, by moving the object in translation, along the optical axis of the device, with reference to the optical system or with respect to the lens close to the object, which induces a phase rotation of the Fourier transform and scrambling of the speckle. The distance between the object and the focussing means is varied; or the distance, between the object and at least one part of the focussing means, remains fixed, and the distance between, on one hand, the assembly of the object and at least one part of the focussing means and, on the other, at least the coherent source and the detection means is varied. It is also possible to move the object in the object plane, which may be an oscillating movement in the object plane, of an amplitude less than one micrometer.

DETAILED DESCRIPTION OF THE EMBODIMENTS OF THE INVENTION

Figure 1A:
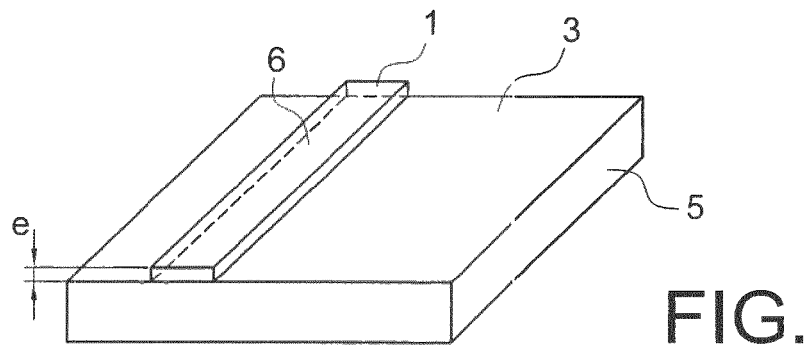
FIGS. 1A-1C represent various objects, each being unique on a substrate.

An example of a unique object used in a method according to the invention is illustrated in FIG. 1A.

The object 1 and the support or substrate 5 thereof are obtained for example from a production unit of components such as those used in microelectronics.

The object 1 rests, or is formed on, the upper surface 3 of the support or substrate 5. For example, it has a non-null thickness or dimension, along a direction perpendicular to said surface 3, whether said thickness is measured above or below (case of channels, FIG. 1C) said surface.

The support or substrate 5 is made of a semiconductor material, for example silicon or SiGe. It may also be a stack of layers such as a SOI. Said substrate 5 may be a wafer as currently used in the field of the semiconductor or microelectronics industry. Such a wafer generally has a dimension or diameter of 200 mm or 300 mm, and a thickness of some tens or hundreds of μm, for example less than 50 μm or 100 μm or 200 μm or 500 μm.

Reference 6 refers to the surface of said unique object, whereon an incident beam will be focussed.

In the example represented, the unique object is a strip 1 on the surface 3 of the substrate 5.

The object 1 is referred to as unique, in that there is no other object on the surface 3 of the substrate 5 at a distance of less than twice the zone illuminated by the incident beam. For example, there is no other object on the surface 3 of the substrate 5 at a distance from the unique object less than twice the diameter or the maximum dimension, measured in the plane of the surface 3, of the zone illuminated by the incident beam. In fact, a single object is addressed during illumination.

The unique object may have other shapes. It may for example be a rectangular (FIG. 1B) or rounded contact block 60, or a channel 61, 62 with a rectangular or rounded cross-section (FIG. 1C). For convenience, two channels are represented in FIG. 1C, but each is in principle unique on the substrate.

For example, the smallest dimension of the object (this dimension is in this case measured perpendicular to the substrate 5) is of the order of 300 nm for a wavelength of approximately 0.4 μm. As a general rule, said minimum dimension is linked with λ. It can be said that both the maximum dimensions and the minimum dimensions are dependent on the wavelength λ, the numerical aperture and the signal-to-noise ratio of the signal measured.

As explained below, the other dimensions are such that they define a surface having a size greater than the size of the spot in the plane 6 of the incident beam 9. For example, the unique object is a contact block 60, for which each of the dimensions d, d' (in this case: the lateral dimensions of the surface of the object whereon focussing takes place) has a minimum value at least equal to 5 nm.

Figure 2:
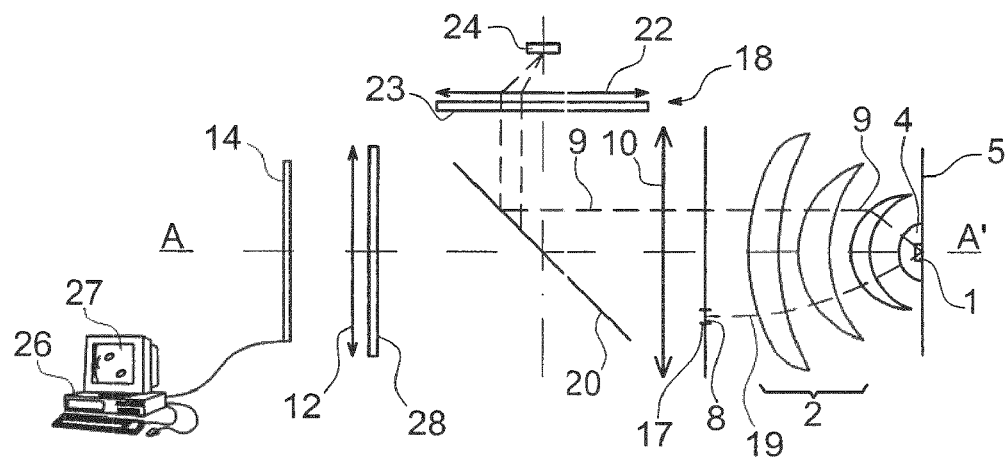
FIG. 2 represents a device according to the invention.

A device and a method are explained in more detail with reference to FIG. 2.

The surface 6 of the object 1 is illuminated using a radiation or a beam 9 from a source 24. The spot of said incident beam 9 from the source is focussed on the surface of the pattern, within the planes parallel with the plane 3. For example, a spot 90, 91, 92 is represented in each of the FIGS. 1A, 1B and 1C; said spot respectively covers the zone delimited by the upper surface of the contact block 60, or a zone or a portion of the channel 61, 62, but also a portion of the substrate 5 which provides a phase reference.

Means (for example a lens assembly) forming a measurement objective 2 used to form the image of the Fourier transform of the surface 6 of the unique object 1 in the image focal plane 8 of said objective. The surface of the object and a part or a zone in the vicinity of the object are illuminated, giving a phase reference. Preferentially, the surface of the object and the adjacent surface are illuminated roughly equivalently.

The optical Fourier transform (OFT) is an optical method used to image the angular response of an object to luminous excitation. Therefore, the invention makes it possible to view this angular response of the light reflected or diffracted by the object.

A transfer objective 10, 12 then forms the image of the Fourier transform of the surface 6 on a sensor 14 formed of detectors.

Said transfer objective comprises for example a pair of lenses 10, 12. The lens 10 may be a field lens.

The sensor 14 is for example a CCD camera. The use of a CCD camera as means 14 for forming an image makes it possible to acquire, in a single acquisition, data equivalent to the number of pixels illuminated by the CCD camera.

Figure 3:
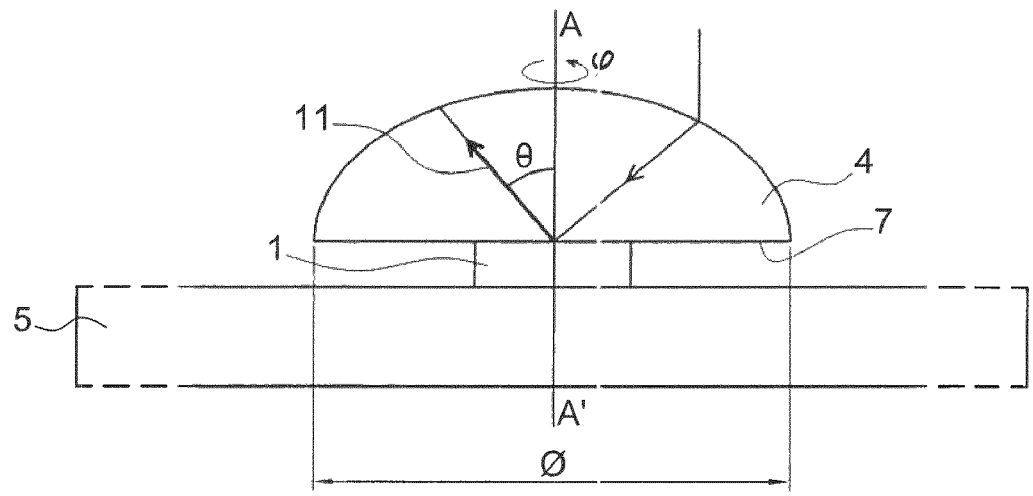
FIG. 3 represents details of a device according to the invention.

The sensor 14 makes it possible to detect the intensity emitted by the surface 6, along each emission direction referenced by the pair (θ, φ) as illustrated in FIG. 3.

This represents a detailed cross-sectional view of the substrate 5, the object 1, the focussing means 4, the incident radiation 9, and the radiation 11 reflected or diffracted by the object according to an angle θ with respect to the optical axis AA' of the system; AA' is defined by the optical axis of the measurement objective 2 and the transfer objective 10, 12.

In the image focal plane 8 (FIG. 2), the distance between the optical axis AA' and the zone 17 where the plane waves emitted from the zone of the surface 6 according to the angle θ is substantially proportional to θ. The azimuth φ corresponds to the azimuth emission direction from said zone of the surface 6.

The illumination may be carried out using a Fourier plane 18 offset from the optical axis AA' of the device via a semi-transparent plane 20. A lens system 22 is arranged on the trajectory of the beam 9 emitted by the source 24 to form a parallel light beam in the Fourier plane 8.

Said radiation source 24 is a coherent source which may be a bright point source such as a laser or a quasi-point source such as a super-radiant LED. It is preferentially positioned at the focal point of an optical system 22 with a sufficiently great focal length such that the diameter of the beam covers all or the majority of the Fourier plane.

The incident beam 9 of the source 24 is focussed on the unique object 1 by the focussing means of the system 2 arranged on the trajectory of said beam.

A lens 4 is arranged in contact either with the object 1 or in quasi-contact with said object, in a manner very close thereto, at a distance for example less than some tens of manometers, for example less than 10 nm or 50 nm or 100 nm.

Typically, the lens 4 is a spherical lens, with a flat part 7 (see FIG. 3). It may have a diameter Φ of the order of approximately 1 mm. In this case, the object 1 is almost in contact with the flat part 7.

The index of the constituent medium in said lens 4 makes it possible to increase the numerical aperture by reducing the size of the illuminated zone accordingly. Said lens may be made of rutile TiO2 (having an index of 2.6) or diamond (having an index of 2.4).

Said lens is preferentially of the solid immersion type, or SIL, which makes it possible to pass the tunnel barrier for high numerical apertures.

The source may be polarised using polarisation means 23 arranged on the trajectory of the beam 9 from the source 24 in the direction of the object 1. Linear, or circular or radial or toric polarisation of the incident beam 9 may thus be carried out.

Means 28 forming a polarisation device may be arranged on the trajectory of the analysed beam, in the direction of the means 14 used to form an image.

Each of the polarisation means 23, 28 or each polariser may comprise two λ/4, or quarter-wave, strips, arranged consecutively (controlled electrically if required) to address all possible polarisation states (including circular, toric, etc.). Linear polarisers may also be used. Radial states are more generally obtained with ¼ wave strips behind the polarisers, generally made of liquid crystals. The rays from the source 24 are in this case collinear (parallel) with the optical axis AA' on the Fourier plane 8 of the optical system.

The infinite diffraction figure, used to analyse the optical system described above, is very substantially dependent on the shape of the unique object. A method according to the invention makes it possible to analyse the shape of the objects with a precision of a few nanometers. The diffraction figure may be analysed in terms of intensity and polarisation.

Figure 4A:
FIGS. 4A and 5A represent objects used during tests of a method according to the invention.
Figure 5A:
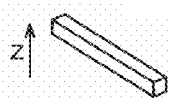
Figure 5B:
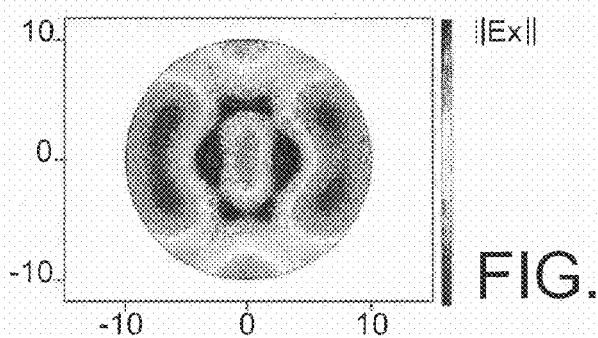
Figure 5C:
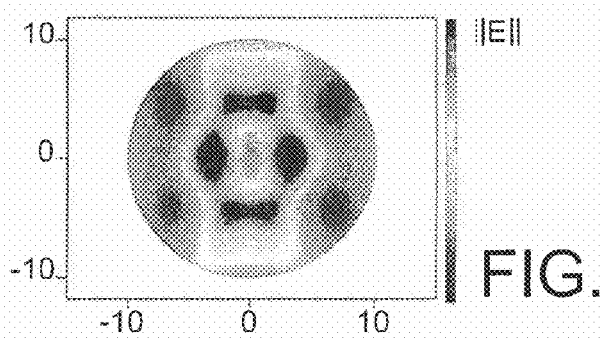
Figure 5D:
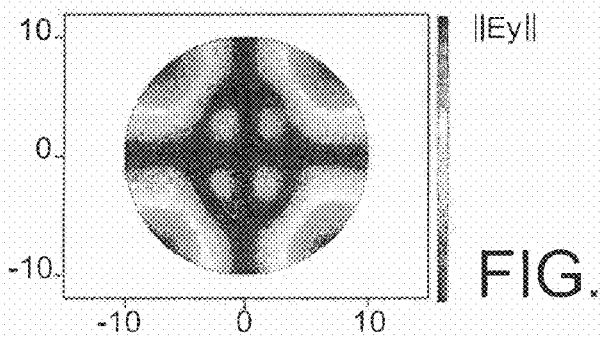

For example, the infinite diffraction figures of 2 cases of unique objects (strip, or parallelepipedic object, as in FIG. 1A) which differ from each other by the thickness thereof are compared: one has thickness e1 of 0.05 μm (measured along the z axis in FIG. 4A, perpendicular to the plane 3 of the substrate 5 whereon the object is formed), the other has a thickness e2 of 0.1 μm (measured along the same z axis, FIG. 5A). The wavelength is 0.5 μm, the index of the SIL lens is 2 and the width of the object is 100 nm.

Figure 4B:
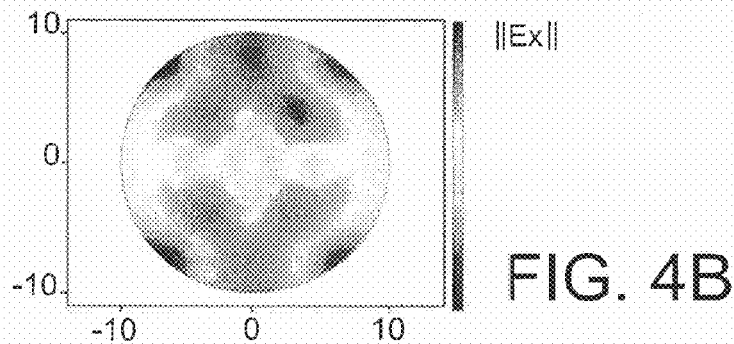
FIGS. 4B-4D and 5B-5D are diffraction images, of the patterns in FIG. 4A and FIG. 4B respectively.
Figure 4C:
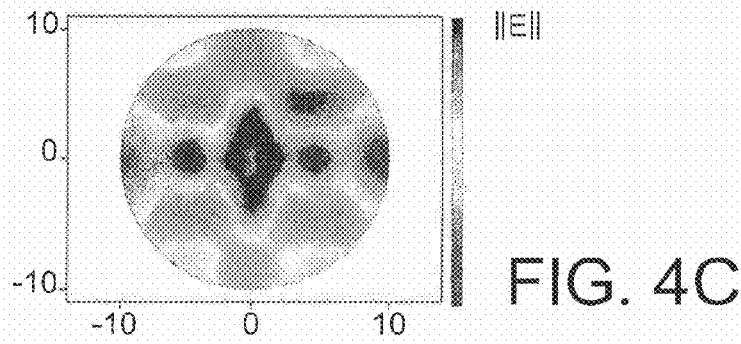
Figure 4D:
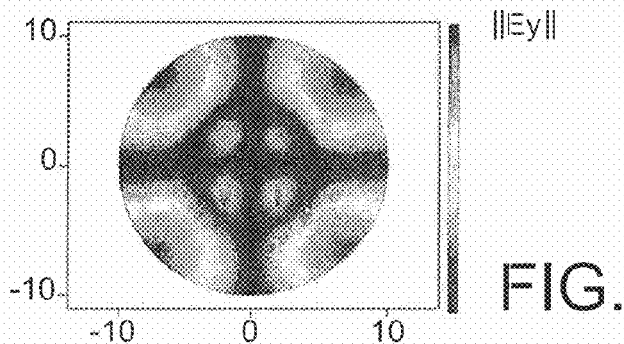

The FIG. 4B (or 5B), 4C (or 5C), 4D (or 5D) represent the quantities ||Ex||, ||E||, ||Ey||, for the object in FIG. 4A (or 5A), i.e. norm of the amplitude of the field along the x axis (defined with respect to the polarisation direction of the incident wave), the intensity of the overall field, and the intensity of the field along the y axis (defined as the direction perpendicular to the polarisation direction of the incident wave).

Between these two objects, a substantial difference in terms of intensity of the distribution of the diffracted field observed in the plane of the pupil of the imager (corresponding to the figures shown) is noted. The polarisation state Ex, used to illuminate the object, and also for detection, is particularly sensitive to the object used, therefore in this case to the thickness of each strip. The information relating to the polarisation Ey is however of interest in that it may differ substantially in terms of intensity according to the shape of the object.

If the shape of the strip varies, the polarisation figure also varies.

Figure 1B:
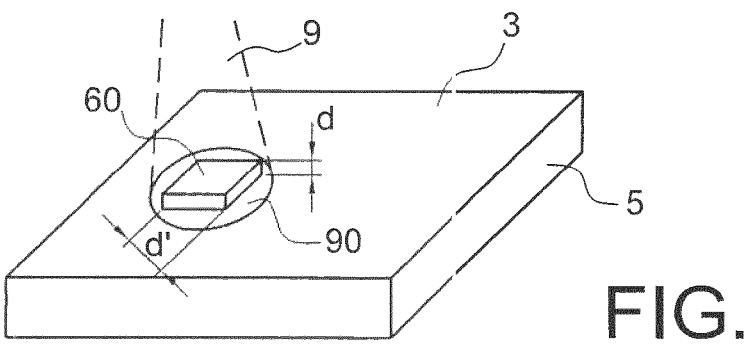
Figure 1C:
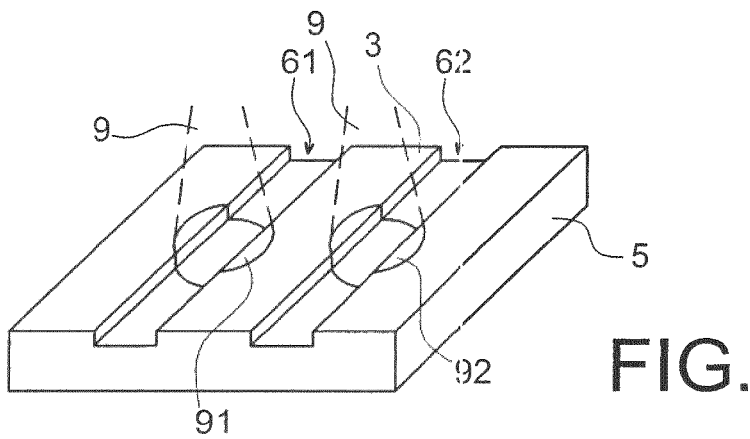

If an object with another shape is used, for example a contact block such as that in FIG. 1B, or a channel (as in FIG. 1C), a different polarisation figure is obtained.

Using digital methods similar to those in "conventional" scaterometry (direct or reverse), enhanced with a polarisation analysis based on spectroscopy as per Muller [C. Brosseau, Fundamentals of Polarized Light, Willey, 1998], it is possible to determine an outline of the shape of the unique object. It is possible to use the FDTD (Finite Difference Time Domain) method and it is possible to loop. For example, a direct calculation is made, using an FDTD method, of the signal diffracted by an object geometry model and a comparison is made with the experimental signal, and a parameter of the geometry is varied to converge by means of successive looping sequences to the most likely geometry, by minimising the "cost" function.

Digital data processing means 26, for example a microcomputer, are used to process the data from the detection means or means used to form the image of the optical FT of the diffracted light 19. These means 26 make it possible for example to produce an image of a diffraction figure, such as that in FIGS. 4B-4D, 5B-5D, that can be displayed on display means 27. In view of the very high sensitivity of the measurement to the shape of the object, an operator may, according to the image perceived, deduce whether the shape is that expected.

It also possible to store in memory, for example in memory means of the means 26, images obtained with specific objects and the shapes of the objects themselves, or data of optical Fourier transform images, and of corresponding objects, said data set forming a database. Then, for each image obtained, a search program makes it possible to identify the most likely object shape. Means for comparing an optical Fourier transform image, produced using an object, with images stored in memory (in the memory storage means of optical Fourier transform image and corresponding object data) may also be provided. In this way, by varying the parameters (looking at the parameter which adjusts the curve in an optimal manner), such a comparison makes it possible to obtain an approximate shape of the object. The display means 27 make it possible to display the image of said shape. As already described above, the sensitivity of the method is such that this approximation may be very satisfactory.

Other data processing operations may be carried out, such as the digital methods described above.

The focussing means 4 are in contact or in quasi-contact with the pattern 1. It is also possible to place an index adaptation liquid (for example ethylbenzene, having an index of 1.49) between said means 4 and the object 1. For example, the index layer has a thickness of approximately 100 nm.

As a general rule, it is desirable to use a wavelength that is as short as possible to increase the influence of the diffraction. For example, a wavelength of approximately 405 nm may be used.

It is also possible to select, as the source 24, a source having a suitable wavelength to resonate with the objects observed (due to plasmon effect, for example).

In the specific case of plasmonic phenomena, preferentially occurring in the red range, it may be advantageous to use a source operating at 650 nm, for example.

The shape of the beam is approximately circular with an intensity distribution which is dependent on the polarisation states selected using the polarisation means 23. The diameter or size of the spot is preferentially less than 1 µm. For example, FWHM (this consists of the full width at half maximum of the intensity curve of the beam in the plane in the vicinity of the surface 6 of the object) is less than 300 nm, taking the field depth into account.

In order to prevent speckle structures associated with the use of a coherent source, particularly in the case of a laser source 24, it is recommended to use means (for example a piezoelectric translation unit) used to carry out a relative movement of the unique object 1 (and, therewith, of the substrate 5), with respect to the optical system, the latter comprising, in the example given, the measurement means 2, 10, 12 (and the means 4). This movement may be oscillating over a range which may be of the order of a fraction of a micrometer, for example less than or equal to 0.1 µm, or 0.5 µm or 1 µm. In fact, a translation in the object plane induces a rotation of the Fourier plane. The phase of the diffracted wave is then subjected to a rotation which scrambles any stationary speckle figure. In fact, it is simply necessary for one of the items to move, and any combination may be obtained as a result.

According to another embodiment, means, such as those for example described in the article by L. P. Ghislain et al., Applied Physics Letters, Vol. 74, no 4, 1999, make it possible to carry out a relative translation between the focussing means 4 and the object 1. Therefore, this translation makes it possible to vary the distance between these two items in the direction of the optical axis AA'. The distance between the lens 4 and the object 1 may change during acquisition. This makes it possible to enhance the signature of the scaterometric signal and break, and therefore eliminate, the coherence.

Another embodiment makes it possible to prevent slippage problems of the surfaces in contact (the surfaces of the lens 4 and of the object 1). According to this other embodiment, the focussing means 4 are separated from the rest of the optical system so that the substrate 5 (with the object 1)—focussing means 4 assembly is moved along the focussing axis AA', relative to the rest of the characterisation device (the amplitude of said movement is of the order of one µm). Means used to carry out this movement are for example piezoelectric means.

The invention may be combined with a production unit of components such as those produced in microelectronics. The object 1 comes from said production unit, passes in front of a device such as that described above with reference to the figures, the data processing means 26 comprising for example a specially programmed micro-computer to implement the processing method as described above. An operator may thus obtain the result of the analysis on the production site itself and modify same accordingly if the analysis indicates different dimensional and/or structural characteristics to those planned.

The invention claimed is:

1. A method of measuring at least one of dimensional or structural characteristics of an object on a substrate, the method comprising:
   forming a coherent radiation beam using a coherent source;
   illuminating the object and a part of a surface of the substrate by the coherent radiation beam so that there is no other object on the surface of the substrate at a distance of less than twice a zone illuminated by the coherent radiation beam, the coherent radiation beam being focussed on the object by a focussing mechanism with a numerical aperture between 0.5 and 3;
   forming, using a detection mechanism, an optical Fourier transform image of light diffracted by the object; and
   measuring, from the optical Fourier transform image, at least one of the dimensional or structural characteristics of the object.

2. The method according to claim 1, wherein the illuminating includes positioning the focussing mechanism at a distance from the object less than 100 nm.

3. The method according to claim 1, wherein a distance between the object and the focussing mechanism is varied.

4. The method according to claim 1, wherein:
   a distance between the object and the focussing mechanism remains fixed, and
   a distance between an object-focussing mechanism assembly and at least the coherent source and the detection mechanism is varied.

5. The method according to claim 1, wherein the object is moved in an object plane.

6. The method according to claim 5, wherein the movement of the object is an oscillating movement in the object plane.

7. The method according to claim 6, wherein the movement of the object has an amplitude less than one micrometer.

8. The method according to claim 1, wherein the coherent source comprises a laser or LED.

9. The method according to claim 1, wherein the object is a contact block, having a rectangular or rounded shape, or a strip, having an elongated shape, or a channel, having a rectangular or rounded or prismatic cross-section.

10. The method according to claim 1, wherein the object and the focussing mechanism are placed in an index adaptation liquid.

11. The method according to claim 1, wherein the coherent radiation beam has a spot having a size, measured on the surface of the substrate, less than one micrometer.

12. A method according to claim 1, wherein the coherent radiation beam has a circular or toric or linear or radial polarization state.

13. The method according to claim 1, further comprising detecting a polarization state of a beam reflected or diffracted by the object.

14. The method according to claim 1, wherein the focussing mechanism comprises a solid immersion lens.

15. A device for measurement of at least one of dimensional or structural characteristics of an object on a surface of a substrate, the device comprising:
   means for illuminating the object by a coherent radiation beam in that there is no other object on the surface of the substrate of less than twice a zone illuminated by the coherent radiation beam;
   means for focusing with a numerical aperture between 0.5 and 3;
   means for forming an image of the optical Fourier transform of light diffracted by the object; and
   means for measuring, from the image of the optical Fourier transform of light diffracted by the object, the at least one of the dimensional or the structural characteristics of the object.

16. The device according to claim 15, wherein the means for focusing comprises a solid immersion type lens.

17. The device according to claim 15, wherein the means to for illuminating the object comprises a laser or LED.

18. The device according to claim 15, further comprising means to vary a distance between (1) an assembly including the means for focusing and (2) the means for illuminating the object and the means for forming the image of the optical Fourier transform of the light diffracted by the object.

19. The device according to claim 15, further comprising means for varying a distance between the object and the means for focusing.

20. The device according to claim 15, further comprising means for moving the object in an object plane.

21. The device according to claim 15, wherein the coherent radiation beam has a spot having a size, measured on the surface of the object, less than one micrometer.

22. The device according to claim 15, further comprising means for polarizing the coherent radiation beam.

23. The device according to claim 15, further comprising means for polarizing a beam reflected or diffracted by the object.

24. The device according to claim 15, further comprising digital means for processing data obtained from the means for forming the image of the optical Fourier transform of the light diffracted by the object.

25. The device according to claim 15, further comprising means for displaying the image of the optical Fourier transform of the light diffracted by the object.

26. The device according to claim 15, further comprising memory that stores an optical Fourier transform image and corresponding object data.

27. The device according to claim 26, further comprising means for comparing the image of the optical Fourier transform of the light diffracted by the object, with images stored in the memory of the optical Fourier transform image and corresponding object data.

28. The device according to claim 25, further comprising means for displaying an image of the object, wherein the image of the optical Fourier transform of the light diffracted by the object approximates the optical Fourier transform image, produced from the object.

* * * * *